United States Patent
Müller et al.

(10) Patent No.: US 8,143,455 B2
(45) Date of Patent: Mar. 27, 2012

(54) PROCESS FOR PREPARING 2-HYDROXYACETALS AND THE CORRESPONDING 2-HYDROXYALKANALS

(75) Inventors: Thomas-Norbert Müller, Monheim (DE); Michael Dockner, Köln (DE)

(73) Assignee: SALTIGO GmbH, Langenfeld, DE (US)

( * ) Notice: Subject to any disclaimer, the term of this patent is extended or adjusted under 35 U.S.C. 154(b) by 0 days.

(21) Appl. No.: 12/665,375

(22) PCT Filed: Jun. 11, 2008

(86) PCT No.: PCT/EP2008/057267
§ 371 (c)(1),
(2), (4) Date: Jun. 16, 2010

(87) PCT Pub. No.: WO2009/000649
PCT Pub. Date: Dec. 31, 2008

(65) Prior Publication Data
US 2010/0280276 A1 Nov. 4, 2010

(30) Foreign Application Priority Data
Jun. 22, 2007 (DE) .......................... 10 2007 028 924

(51) Int. Cl.
*C07C 41/50* (2006.01)
*C07C 45/42* (2006.01)
(52) U.S. Cl. ....................... 568/600; 568/486
(58) Field of Classification Search .................. 568/486, 568/600
See application file for complete search history.

(56) References Cited

FOREIGN PATENT DOCUMENTS
DE  531336  8/1931

OTHER PUBLICATIONS

Kuznetsov, N.V.; Krasavtsev I.; "Glycolaldehyde and its Acetals", Soviet Progress in Chemistry, Bd. 42, 1976, pp. 57-61.
Kuznetsov, N.V.; Krasavtsev, I.; Aleksankin M.M.; "Alcoholysis of 1,2-dibromoethyl acetate", Soviet Progress in Chemistry, Bd. 42, 1976, pp. 64-67.
Wong Ch-H, et al.; "Chemical and Enzymatic Syntheses of 6-Deoxyhexoses Conversion to 2,5-Dimethyl-4-Hydroxy-2, 3-Dihydrofuran-3-One (Furaneol) and Analogues1", Journal of Organic Chemistry, American Chemical Society, Bd. 48, Nr. 20, 1983, pp. 3493-3497.
International Search Report from co-pending Application PCT/EP2008/057267 dated Sep. 2, 2008, 3 pages.

*Primary Examiner* — Sikarl Witherspoon
(74) *Attorney, Agent, or Firm* — Michael A. Miller

(57) ABSTRACT

What is described is a process for preparing 2-hydroxyacetals of the general formula in which $R^1$ is hydrogen, a branched or unbranched $C_1$-$C_{12}$-alkyl radical, an electron-deficient, halogen-, $NO_2$—, $CN$—, $CF_3$—, acyl group- or branched or unbranched alkyl group-substituted or unsubstituted $C_5$-$C_6$-aryl or heteroaryl, and $R^2$ is a branched or unbranched $C_1$-$C_5$-alkyl radical, or both $R^2$ radicals are bonded directly to one another or to one another via a $C_1$-$C_4$ unit, by reacting an enol compound of the general formula (II) in which $R^3$ is the same and $R^1$ is as defined for formula (Ia), with bromine to give the corresponding dibromo adduct and then reacting this dibromo adduct with an alkoxide of the general formula (III) M-O—$R^2$ (III) in which $R^2$ is as defined for formula (Ia) and O is oxygen and M is lithium, sodium or potassium. What is likewise described is the preparation of the corresponding 2-hydroxyalkanals from the 2-hydroxyacetals thus obtained by acidic hydrolysis.

6 Claims, No Drawings

PROCESS FOR PREPARING 2-HYDROXYACETALS AND THE CORRESPONDING 2-HYDROXYALKANALS

The invention relates to a novel process for preparing 2-hydroxyacetals and the corresponding 2-hydroxyalkanals. 2-Hydroxyalkanals and 2-hydroxyacetals, for example 2-hydroxyhexanal and the dimethyl acetal thereof, constitute important intermediates for the synthesis of active pharmaceutical ingredients.

Houben-Weyl, Vol. E6b1, p. 40 ff., describes the state of the art regarding preparation of benzofurans. The more recent literature includes examples of cyclization of 2-phenoxyalkanals or 2-phenoxyacetals (Kwiecien, *Synth. Commun.* 2005, 35, 2223-2230, and *J. Pol. Chem.* 2004, 78, 249-254). The starting materials are prepared by Rosenmund reaction of the corresponding carbonyl chlorides. The preceding etherification step has to be performed under very severe conditions for more sterically demanding substrates.

2-Hydroxy dimethyl acetals are generally obtained by reacting the corresponding α-haloaldehydes with methanol in the presence of sodium methoxide. *The Chemistry of α-Haloketones, α-Haloaldehydes and α-Haloimines* (Wiley), p. 369 ff. summarizes all existing results regarding preparation and reaction of α-haloaldehydes up to 1988. In general, the halogenating agent (bromine or sulfuryl chloride) is introduced at not more than 10° C. into the aldehyde diluted with methylene chloride or carbon tetrachloride. The yields are typically between 30 and 50%. The reaction of the reaction product with sodium methoxide in dry methanol leads to the hydroxyacetal in 40-70% yield after distillative purification of the crude product.

More recent synthesis routes generate α-hydroxyacetals by reaction of aldehydes with a stoichiometric amount of iodine in alkaline methanol solution (Zacuto, *Tetrahedron Lett.* 2005, 46, 447-450). In addition, α-haloacetals can be converted to α-hydroxyacetals by conversion to the corresponding hemiacetal acetate and subsequent reaction with lithium methoxide in high dilution (Ghelfi, *Tetrahedron* 1994, 50, 7897-7902).

One means of synthesizing glycolaldehyde dimethyl acetal includes the reaction of vinyl acrylate with bromine at low temperatures, followed by the treatment of the bromo adduct with sodium methoxide (Komarova, *J. Org. Chem. USSR (Engl. Transl.)* 1977, 2146-2148). However, the reaction is performed in solvents which cannot be used on the industrial scale, such as carbon tetrachloride or diethyl ether; furthermore, the product was obtained after distillation only in yields of 44-51%.

It was an object of the present invention to discover a new, more economically viable route to preparation of 2-hydroxyacetals and the corresponding 2-hydroxyalkanals with improved yield and simplified performance.

A process has now been found, in which, by reaction of an enol compound with bromine and subsequent further reaction of the bromo adduct with an alkoxide, 2-hydroxyacetals and 2-hydroxyalkanals become obtainable.

This reaction sequence has not yet been followed to date for the preparation of 2-hydroxyalkanals.

The invention therefore provides a process for preparing 2-hydroxyacetals of the general formula (Ia)

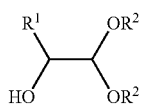
(Ia)

in which
R¹ is hydrogen, a branched or unbranched $C_1$-$C_{12}$-alkyl radical, an electron-deficient $C_5$-$C_6$-aryl or heteroaryl radical which is unsubstituted or substituted by halogen, an —$NO_2$, —CN, —$CF_3$ or acyl group or a branched or unbranched alkyl group, and R² is a branched or unbranched $C_1$-$C_5$-alkyl radical, or the two R² radicals are bonded directly to one another or via a $C_1$-$C_4$ unit, by reacting an enol compound of the general formula (II)

(II)

in which
R³ is

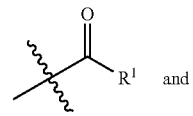
and

R¹ is as defined for formula (Ia)
with bromine to give the corresponding dibromo adduct and then reacting this dibromo adduct with an alkoxide of the general formula (III)

(III)

in which
R² is as defined for formula (Ia) and
O is oxygen and
M is lithium, sodium or potassium.

The dibromo adduct of the enol compound of the formula (II) is preferably reacted with one another with the alkoxide of the formula (III) in a so-called one-pot process without a further purification step.

The specific procedure is to initially charge the enol compound and to cool it to 0 to 10° C., especially 3 to 7° C. Subsequently, the bromine is metered in such a way that the temperature of the reaction mixture is kept between 0 and 10° C., especially between 3 and 7° C. The total metering time is typically between 0.5 and 3 hours, preferably 2 hours. Subsequently, the reaction mixture can then be used directly in the next step without further workup and purification.

The next step is performed by initially charging between 1.5 and 4 equivalents, especially between 2 and 3 equivalents, of alkoxide, especially the sodium methoxide in dry methanol (methoxide content in methanol 10 to 30% by weight, especially 25 to 30% by weight), and cooling it to 10° C. Subsequently, 1 equivalent of the dibromo adduct of the enol compound of the formula (II) is metered in such a way that the temperature of the reaction mixture is between 10 and 30° C., especially between 15 and 25° C. The metering times are between 0.5 and 4 hours, especially between 1.5 and 2.5 hours. On completion of metered addition, the mixture is then stirred at 20 to 40° C. for a further 0.5 to 2 hours, and then the alcohol used as the solvent, typically methanol, is distilled off under reduced pressure at 50 to 60° C. After the salts have been washed out, the resulting product is obtained by the process according to the invention usually in a purity of 94 to 96% (GC) in a yield of 80 to 90%, based on the enol compound of the formula (II) used. If desired, the 2-hydroxyacetal prepared in accordance with the invention can be purified further by means of vacuum distillation. If it is necessary to use the product in solution in the subsequent step, the reaction mixture, after the metered addition into the alkoxide solution, can be discharged onto boiling water, and the alcohol used as the solvent, typically methanol, can be distilled off simultaneously. Subsequently, the aqueous phase can be extracted with a suitable water-immiscible solvent such as toluene, chlorobenzene or xylene.

In the 2-hydroxyacetals prepared by the process according to the invention, $R^1$ is preferably a $C_4$-alkyl or phenyl radical. $R^1$ may, though, also be a $C_5$-$C_6$-aryl or heteroaryl radical substituted, for example, by a halogen, or a —CN, —NO$_2$, —CF$_3$, acyl or alkyl group, for example ethyl or isopropyl. Unsubstituted aryl radicals such as phenyl, or branched and unbranched $C_1$-$C_{12}$-alkyl radicals, are also possible.

$R^2$ may be a branched or unbranched $C_1$-$C_{12}$-alkyl radical, for example methoxide, ethoxide, propoxide, isopropoxide, sec- or tert-butoxide or amylate radical. The two $R^2$ radicals may also be bonded directly to one another or via a $C_1$-$C_4$ unit.

$R^2$ is especially a methyl or ethyl group, and the compounds of the general formula (Ia) are thus a 2-hydroxy dimethyl acetal or 2-hydroxy diethyl acetal.

In a preferred mode of operation, the process according to the invention is performed without the addition of a solvent.

By acidic hydrolysis, it is possible to convert the 2-hydroxyacetals prepared in accordance with the invention easily to the corresponding 2-hydroxyalkanals. The hydrolysis is preferably performed immediately after the preparation of the 2-hydroxyacetals by adding a 10% citric acid solution to the reaction solution. The preparation of the corresponding 2-hydroxyalkanals from the 2-hydroxyacetals obtained in accordance with the invention therefore likewise forms part of the subject-matter of this invention.

The yields achieved by the process according to the invention considerably exceed the yields obtained by known processes. Furthermore, the purities achieved make a distillative purification of the product superfluous. Product losses which inevitably occur as a result of complex purification and distillation of this sensitive product class can thus advantageously be avoided.

According to the existing prior art, the inventive synthesis route to 2-hydroxyacetals and -alkanals has to date not been taken in this way, since it has always been assumed to date that the direct synthesis via the corresponding enol compound to give the corresponding alkanal or acetal compounds is impossible apart from a few exceptions.

It is therefore all the more surprising that such high yields and purities can be achieved by the process according to the invention. The examples which follow are intended to further illustrate the invention, but without restricting its scope.

EXAMPLES a) Bromination Step

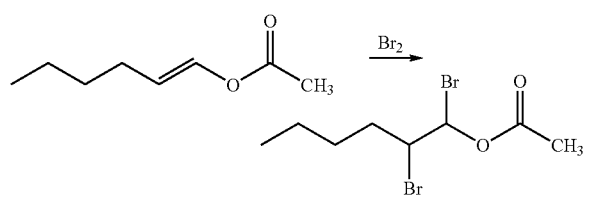

A 1 l flat-flange vessel was initially charged with 168 g (1.17 mol, 1.0 eq) of hexenyl acetate and cooled to 5° C. Subsequently, 189 g (1.17 mol, 1.0 eq) of bromine were metered in such that the temperature of the reaction mixture was kept between 0-10° C. The total metering time was between one hour and three hours. The reaction mixture was used directly in the next step without further workup and purification, or stirred at 5° C. for a further 2 hours before further use. 354 g of the desired dibromo adduct precipitated out as a pale yellow to pale brown liquid.

b) Hydroxylation Step

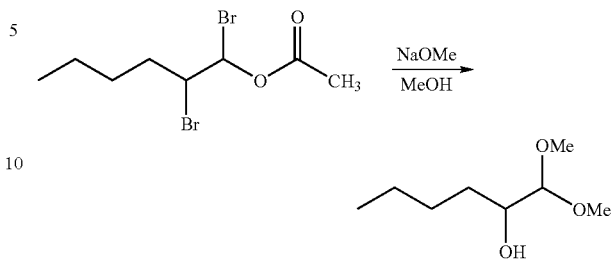

A 1 l flat-flange vessel was initially charged with 2 equivalents of sodium methoxide solution in methanol (30% by weight) and cooled to 10° C. Subsequently, 1 equivalent of the dibromo adduct was metered in such that the temperature of the reaction mixture was between 10 and 20° C. Immediately after the start of metered addition, the formation of a colorless solid was observed. The metering time was 2.5 hours. On completion of metered addition, stirring was continued at 25° C. for 2 hours and then, at internal temperature 55° C. and vacuum 350 mbar, 250 ml of methanol were distilled off. The mixture was cooled to 25° C. and then 300 ml of water were added. The aqueous phase is removed and the organic phase washed twice with 100 ml of water each time. The desired product was obtained as a pale brown liquid in 95% purity (GC) in 8.5% yield.

The invention claimed is:

1. A process for preparing 2-hydroxyacetals of the general formula (Ia)

(Ia)

in which
$R^1$ is hydrogen, a branched or unbranched $C_1$-$C_{12}$-alkyl radical, an electron-deficient $C_5$-$C_6$-aryl or heteroaryl radical which is unsubstituted or substituted by halogen, an —NO$_2$, —CN, —CF$_3$ or acyl group or a branched or unbranched alkyl group, and
$R^2$ is a branched or unbranched $C_1$-$C_5$-alkyl radical, or the two $R^2$ radicals are bonded directly to one another or via a $C_1$-$C_4$ unit,
by reacting an enol compound of the general formula (II)

(II)

in which
$R^3$ is

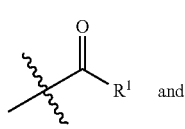

$R^1$ and $R^1$ is as defined for formula (Ia)
with bromine to give the corresponding dibromo adduct and then reacting this dibromo adduct with an alkoxide of the general formula (III)

M-O—$R^2$ (III)

in which

R² is as defined for formula (Ia) and

O is oxygen and

M is lithium, sodium or potassium, wherein the dibromo adduct of the enol compound is metered in at a reaction temperature between 10 and 30° C. over a reaction time of 0.5 to 4 hours and the mixture is then stirred at 20 to 40° C.

2. The process as claimed in claim 1, characterized in that the dibromo adduct of the enol compound of the formula (II) is reacted with the alkoxide of the formula (III) without a further purification step.

3. The process as claimed in claim 1, characterized in that R¹ is a $C_4$-alkyl radical or a phenyl radical.

4. The process as claimed in claim 1, characterized in that R² is a $C_1$- or $C_2$-alkyl radical.

5. The process as claimed in claim 1, characterized in that the bromine is metered into enol compound of the formula (II) at a reaction temperature between 0 and 10° C.

6. The process as claimed in claim 1, characterized in that the reaction proceeds without the addition of a further solvent.

* * * * *